(12) United States Patent
Rice

(10) Patent No.: US 6,552,242 B1
(45) Date of Patent: Apr. 22, 2003

(54) FRACTIONATION IN LIGHT PARAFFIN ISOMERIZATION PROCESS

(75) Inventor: Lynn H. Rice, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/948,979

(22) Filed: Sep. 7, 2001

(51) Int. Cl.[7] .............................. C07C 7/00; C07C 7/04; C07C 7/11; B01D 3/14; C10G 7/00

(52) U.S. Cl. .................. 585/800; 585/802; 585/820; 585/825; 208/347; 208/350

(58) Field of Search ................................ 585/800, 802, 585/820, 825, 719; 208/347, 350

(56) References Cited

U.S. PATENT DOCUMENTS

| | | | |
|---|---|---|---|
| 2,921,104 A | 1/1960 | Haensel | 260/683.25 |
| 4,717,784 A | 1/1988 | Stem et al. | 585/738 |
| 4,804,802 A | 2/1989 | Evans et al. | 585/734 |
| 5,026,951 A | 6/1991 | Schmidt et al. | 585/738 |
| 5,043,525 A | 8/1991 | Haizmann et al. | 585/737 |
| 5,107,052 A | 4/1992 | McCulloch et al. | 585/738 |

*Primary Examiner*—Thuan D. Dang
(74) *Attorney, Agent, or Firm*—John G. Tolomei; James C. Paschall; David J. Piasecki

(57) ABSTRACT

Fractional distillation performed to recover butane used as a desorbent component for adsorptive separation is integrated with the other fractionation of the raffinate stream of a $C_5$–$C_6$ paraffin adsorptive separation zone. A single fractionation column is employed to recover the desorbent butane, a highly branched paraffin product stream and a mono-branched paraffin rich recycle stream, thus reducing the cost of the process.

6 Claims, 2 Drawing Sheets

FRACTIONATION IN LIGHT PARAFFIN ISOMERIZATION PROCESS

FIELD OF THE INVENTION

The invention relates to a process for the isomerization of light paraffins, such as pentanes and hexanes, to produce more highly branched paraffins of higher octane number and greater utility as naphtha boiling range motor fuel. The invention specifically relates to an improvement in the fractional distillation scheme used to recover a $C_4$ desorbent, a recycle stream and a product stream from an effluent of an adsorptive separation zone used to recover the highest octane paraffins.

BACKGROUND OF THE INVENTION

The majority of the naphtha boiling range hydrocarbons recovered from petroleum do not have the high octane numbers desired for modern gasolines. For instance, straight chain or relatively straight chain $C_5$ and $C_6$ hydrocarbons have an octane number which is lower than desired for gasoline blending components. As a result it is necessary for modern petroleum refineries to build high octane molecules, as by alkylation, and to increase the octane of existing straight chain molecules by isomerization. By isomerizing these straight chain molecules to more highly branched molecules the octane number of the molecules is increased.

Isomerization of naphtha boiling range hydrocarbons is affected by contacting the hydrocarbons with an isomerization catalyst at isomerization conditions. Unfortunately, such isomerization steps do not result in a complete conversion of the straight chain feed molecules, and a sizable percentage of the isomerate or product of this contacting consists of molecules which have only a moderate increase in branching. In order to further increase the octane of the product it is therefore necessary to separate out and recycle the relatively less branched and therefore lower octane hydrocarbons to the isomerization zone. This separation step can be performed by fractional distillation but adsorption is more effective in performing a division between the close boiling low and high octane molecules. The subject invention relates to fractional distillation steps performed as part of an adsorptive separation used in the recovery of high octane hydrocarbons for the purpose of recycling low octane hydrocarbons to an isomerization zone.

RELATED ART

The commercial benefit of isomerizing normal paraffins to increase their octane has led to the development of a number of separatory schemes and techniques. The integration of isomerization and adsorption is described for instance in U.S. Pat. No. 2,921,104 issued to V. Haensel and in U.S. Pat. No. 4,717,784 issued to S. C. Stem et. al. The process of this latter reference employs an adsorbent comprising a ferrierite molecular sieve to produce a normal paraffin recycle stream to an isomerization zone. Monomethyl branched paraffins are also recycled.

U.S. Pat. No. 5,026,951 issued to R. J. Schmidt et. al. illustrates a process flow comprising an isomerization zone and a simulated moving bed adsorptive separation zone for the recovery of high octane $C_6$ hydrocarbons and the recycling of low octane hydrocarbons. The raffinate (unadsorbed) effluent of the adsorptive separation zone is passed into a raffinate column to generate a desorbent stream and the recycle stream. This reference describes the use of n-butane as a desorbent, with n-butane being removed overhead in the raffinate column and recycled to the adsorption zone. U.S. Pat. No. 5,107,052 issued to B. McCulloch et. al. also illustrates this sequential flow but employs aluminophosphate adsorbents and a C6–C10 normal paraffin desorbent, such as normal heptane.

U.S. Pat. No. 4,804,802 issued to W. E. Evans et al., also describes the separation of a hydrocarbon feed by adsorption, with normal paraffins being recycled separately from a recycle stream comprising both normal and monomethyl paraffins. Two adsorbents are employed in series flow to accomplish this. A product of more highly branched paraffins is recovered.

U.S. Pat. No. 5,042,525 issued to R. S. Haizmann et. al. presents a variation of the combined adsorption-isomerization process for producing high octane $C_6$ hydrocarbons. The isomerization zone effluent flows into an adsorptive separation zone, and the raffinate of the adsorptive separation zone flows into a midpoint of a deisohexanizer column. Desorbent normal hexane is removed from this column as a sidecut and recycled.

SUMMARY OF THE INVENTION

The invention is an improved configuration of the fractional distillation zone used downstream of an adsorption zone which is separating paraffinic hydrocarbons. The invention reduces the capital and utility costs of this fractional distillation zone by combining two prior art columns into one column.

A broad embodiment of the invention may be characterized as a process for recovering high octane, di-branched paraffins from the raffinate stream of an adsorptive separation process, which process comprises passing a raffinate stream removed from an adsorptive separation zone, which stream comprises a desorbent hydrocarbon, mono-branched paraffins and di-branched paraffins, into a fractional distillation column maintained at fractionation conditions, with said column having an intermediate section divided into adjoining first and second vertical fractionation chambers by a substantially flow preventing vertical dividing wall, with the column also containing an upper first full diameter fractionation section located above the intermediate section and a lower second full diameter fractionation section located below the intermediate section; recovering a first product stream rich in mono-branched paraffins from the second full diameter fractionation section; allowing vapor to pass upward from the second full diameter fractionation section into the first vertical fractionation chamber, and allowing vapor to pass upward from the first vertical fractionation chamber into the first full diameter fractionation section; removing an overhead vapor stream comprising the desorbent hydrocarbon from the first full diameter fractionation section, and recovering a second product stream comprising the desorbent hydrocarbon; passing liquid comprising di-branched paraffins and the desorbent hydrocarbon downward from the first full diameter fractionation section into the second vertical fractionation chamber; recovering a second product stream comprising di-branched paraffins from a lower portion of the second vertical fractionation chamber.

DETAILED DESCRIPTION OF THE PREFERRED EMBODIMENTS

Figure 1:
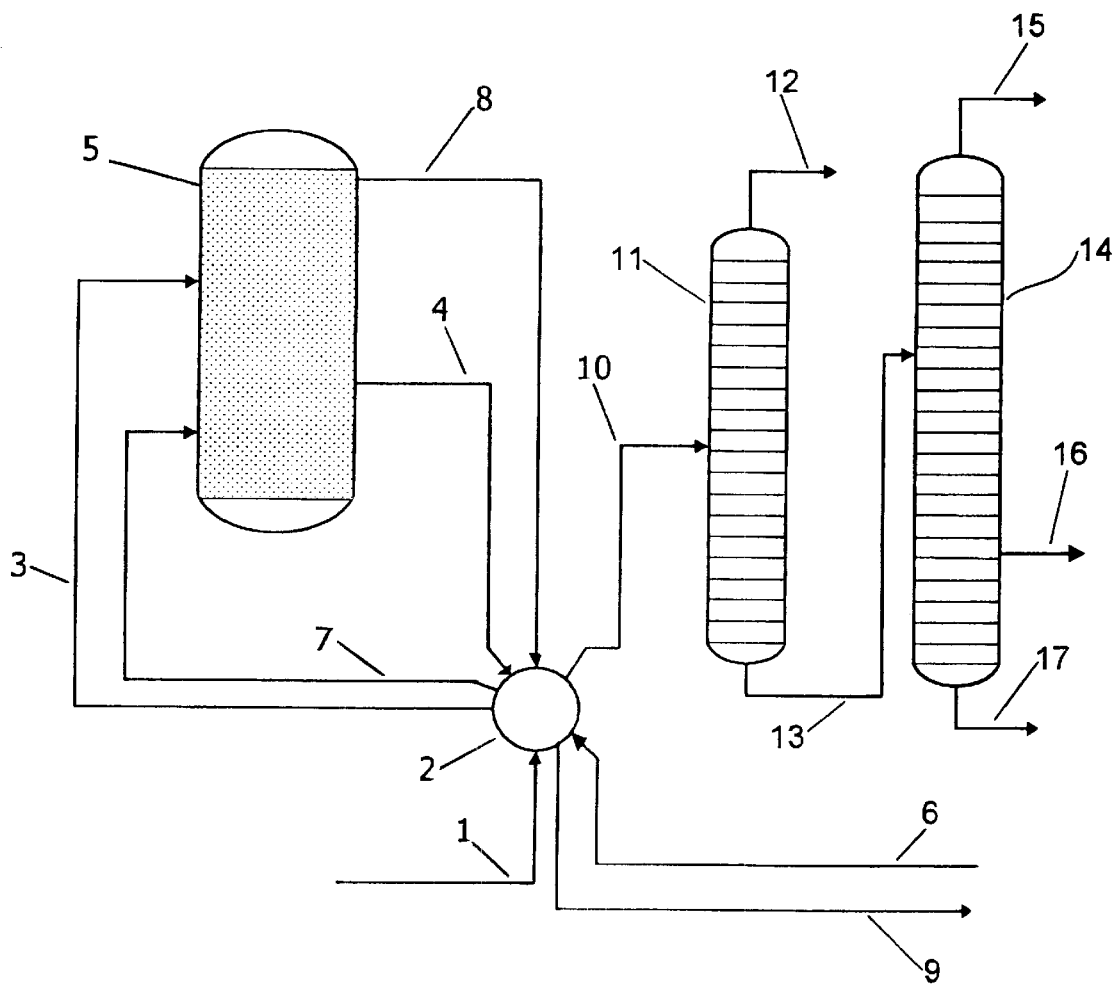
FIG. 1 is a simplified process flow diagram of a simulated moving bed adsorptive separation process employing a prior art two fractionation column arrangement to separate the raffinate stream removed from the adsorption chamber 5.

As pointed out above, an isomerization zone can be employed to increase the octane number of the hydrocarbons in a naphtha boiling range paraffin fraction recovered from petroleum. These hydrocarbons, which are separated in the subject process, generally have from 5 to 7 carbon atoms per molecule although some $C_4$ and $C_8$ hydrocarbons may be present. Preferably the feed is substantially free of $C_4$ hydrocarbons. The petroleum-derived fraction will contain a mixture of normal and isoparaffins, with the isoparaffins including mono-, di-, and tri-branched paraffins. It may also contain some coboiling cyclic hydrocarbons. The paraffinic hydrocarbons will range in octane number from low octane straight chain paraffins, such as normal hexane, to high octane more highly branched paraffins, such as dimethyl butane. The octane number of this raw fraction is often fairly low. To upgrade this raw mixture to a higher octane number blending component for use in a modern gasoline, the mixture is charged to an isomerization zone. To achieve the highest possible octane product, the lower octane number components of the isomerization zone effluent are removed and recycled to the isomerization zone. This can be done to some extent by fractional distillation but adsorptive separation based upon hydrocarbon structure is much more effective. This is due in part to the large number of different hydrocarbons present in the isomerization zone effluent and their close boiling points.

The effluent of a light paraffin isomerization zone is therefore often passed into an adsorptive separation zone. In the adsorptive separation zone the isomerization zone effluent is brought into contact with a solid adsorbent which is selective for either the straight chain molecules or the non-straight chain molecules. The selectively retained hydrocarbons, assumed herein to be the normal and mono-branched paraffins, are then removed from the adsorbent by contacting it with a compound which is more highly adsorbed and which thereby functions as a desorbent for the normal and branch chain paraffins. The desorbent is normally a different hydrocarbon which is compatible with the hydrocarbons being processed and different enough in boiling point to allow easy separation by fractional distillation. The hydrocarbons removed from the adsorbent by the desorbent exit the adsorption zone in a stream referred to as the extract stream It will contain a mixture of the selectively adsorbed hydrocarbons and the desorbent hydrocarbon(s). The hydrocarbons which are not adsorbed onto the adsorbent continue through the adsorbent and are removed from the adsorption zone as a stream referred to herein as the raffinate stream. The raffinate stream will also contain some desorbent hydrocarbons due to the presence of desorbent in the pores of the adsorbent and in the void spaces between adsorbent particles before contact with the feed stream. The subject invention is useful in the separation of these mixtures of naphtha boiling range paraffins and desorbent produced in an adsorptive separation zone. The separation is preformed for two reasons. First, there is the recovery of the desorbent for reuse in the adsorption zone. It is also normally desired to remove it from the streams being discharged since the desorbent will not normally fall within the naphtha boiling point range. It may also be of low octane. Second, the effluent streams, especially the raffinate stream is separated to allow recycling the lower octane components, such as methyl pentanes, to the adsorption zone allowing for the production of a higher octane number product.

Adsorptive separation zones are well described in the art and conventional systems and methods can be employed in the practice of the invention. The adsorptive separation zone can employ a single fixed bed of adsorbent or multiple fixed beds of adsorbent operated in a once-through or cyclic mode of operation wherein the entire bed is cycled between adsorption and regeneration. However, it is greatly preferred that the separatory technique of the subject invention is employed in conjunction with a simulated moving bed adsorptive separation process such as described in the previously cited references. Either liquid or vapor phase adsorption may be employed, with liquid phase being preferred. An adsorbent comprising a type 5A molecular sieve may be employed.

The isomerization technology may also be of conventional nature.

The feed and recycle hydrocarbons are preferably contacted with an isomerization catalyst maintained at isomerization conditions preferably in the presence of a limited but positive amount of hydrogen as described in U.S. Pat. Nos. 4,804,803 and 5,326,296. Isomerization conditions in general include a temperature of from about 95 to 260° C. The isomerization catalyst may be amorphous e.g. based upon amorphous alumina or zeolitic. A zeolitic catalyst would still normally contain an amorphous binder. The catalyst may comprise a sulfated zirconia and platinum as described in U.S. Pat. No. 5,036,035 and European patent application 0 666 109 A1 or a platinum group metal on chlorided alumina as described in U.S Pat. No. 6,214,764. Another suitable catalyst is described in U.S. Pat. No. 5,922,639. These references are incorporated herein for their teaching as to catalyst compositions, isomerization operating conditions and techniques. Operating temperature depends upon the feed composition and catalyst activity. It is usually between about 40 to 160° C. Operating pressure is usually maintained within the range of 2 to 3.5 MPa, with the reactor being operated at an overall L.H.S.V. of about 0.5 to 5 $hr^{-1}$.

Figure 2:
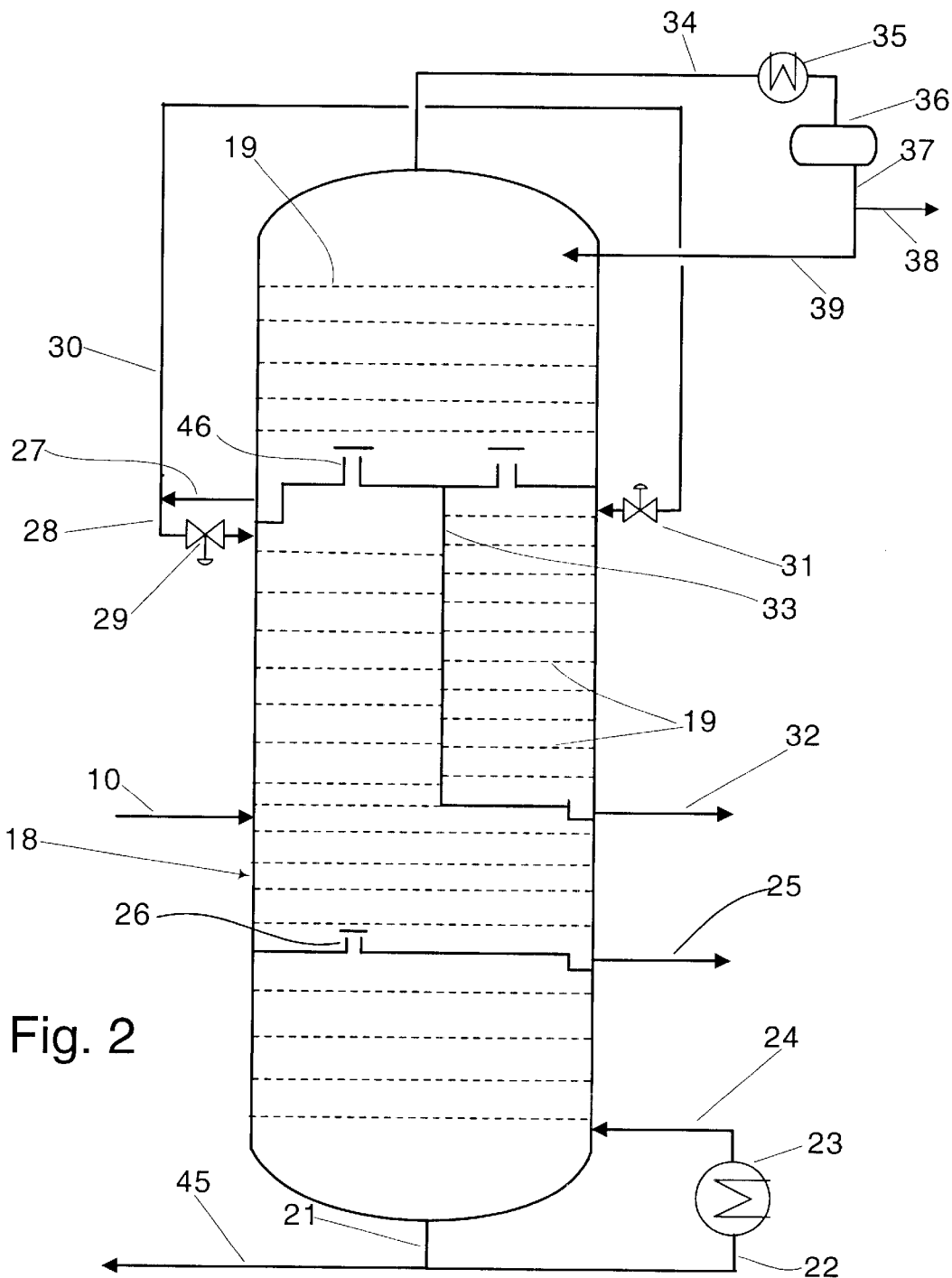
FIG. 2 is a depiction of a single fractionation column according to the invention, which replaces the two columns of FIG. 1.

Referring now to FIG. 1, there is shown a simplified flow diagram of a simulated moving bed adsorptive separation process which has as its main elements a rotary valve 2, an adsorbent chamber 5, and two fractionation columns 11 and 14. FIG. 1 illustrates a representative prior art simulated moving bed adsorptive separation zone together with the two fractionation columns of the fractionation zone located downstream of the separation zone for the separation of the raffinate stream of the adsorption zone. It does not show other fractionation which may be employed in the process. This representation and that of FIG. 2 are presented to illustrate the overall utility and usage of the invention and are not intended to limit its application to any one form of adsorptive separation or mechanical construction of the column.

A feed stream comprising a mixture of acyclic paraffins and a very small amount of co-boiling cyclic paraffins, such as a stabilized effluent of a paraffin isomerization zone, enters the process through line 1. Line 1 directs this entering stream into the rotary valve 2 which in turn passes the feed stream into one of a number of bed lines extending from the rotary valve 2 to the adsorbent chamber 5. A single adsorbent chamber 5 is shown on the drawing. However, some commercial applications of SMB process technology employ two such chambers. For purposes of simplicity only one of the bed lines utilized for passage of the feed stream into the adsorption chamber is illustrated. A representative commercial adsorptive separation chamber would have about 8 bed lines leading to different subbed locations in the chamber. The rotary valve steps the passage of the feed stream through each of these bed lines in turn as part of the simulation of the movement of the adsorbent. In a similar manner, the other bed lines used to simultaneously carry a desorbent stream to the adsorbent chamber and to remove extract and raffinate streams are also stepped along the length of the chamber. That is, the location at which the relevant process stream enters or leaves the adsorbent chamber, is incrementally moved along the length of the adsorbent chamber. This technique is well described in the art and used commercially.

For purposes of illustration it is assumed the feed stream of line 1 is transferred by the rotary valve 2 into a bed line 7, which then carries it into the adsorbent chamber 5. The feed stream is distributed across the horizontal cross section of the cylindrical adsorbent bed by a distribution/collection means not shown and then passes vertically through an adsorption zone comprising several sub-beds of adsorbent before emerging as raffinate withdrawn from the adsorbent chamber 5 through line 8. Each incremental movement or step of the bedlines adds a new sub-bed to one end of the adsorption zone and removes a different sub-bed of adsorbent from the other end of the adsorption zone. During passage through the adsorbent the normal paraffins in the feed stream are selectively retained by the solid adsorbent in the chamber. The unadsorbed molecules become part of the raffinate stream. The raffinate stream is, therefore, much enriched in the isoparaffins originally present in the feed stream of line 1. The raffinate stream of line 8 will also contain some desorbent material which is present in the void volume being swept by the feed stream or which is released from the adsorbent during the adsorption process. The raffinate stream of line 8 therefore comprises an admixture of desorbent compounds and the residual components of the feed stream, which will be basically non-normal hydrocarbons. The raffinate stream may contain some normal paraffins with this amount varying with the degree of recovery achieved in the adsorbent bed. The adsorption zone is normally designed to retain at least 90 mol percent of the normal paraffins present in the feed stream.

The passage of the feed stream through the adsorbent located in the sub-beds forming the adsorption zone results in this adsorbent becoming saturated or "loaded" with the normal paraffins. A stream of desorbent is passed into the process through line 6 and then passed through bed line 3 into the adsorbent chamber 5. The desorbent is also distributed across the cross section of the adsorbent bed and then passed horizontally downward through several different sub-beds of adsorbent, which together form a desorption zone. This adsorbent was previously part of the adsorption zone and is thus initially loaded with normal paraffins. Contact of this adsorbent with the desorbent releases the normal paraffins. The desorbent and the paraffins which it displaces from the adsorbent are removed from the chamber as an extract stream carried by yet another bed line 4. Bed line 4 carries the extract stream to the rotary valve 2 which delivers it to line 9. From line 9 the extract stream flows into a fractionation column not shown for recovery of desorbent and the normal paraffins, which are typically passed into the isomerization zone as a recycle stream.

The raffinate stream is removed from the rotary valve 2 via line 10 and passed into a stripping column often referred to in the art as the raffinate column. In this column the lower boiling desorbent compounds, preferably $C_4$ paraffins, are removed as an overhead stream via line 12. The remaining $C_5^+$ components of the raffinate stream are collected as the net bottoms stream of column 11 and passed through line 13 into a deisohexanizer column 14.

Two separate fractionation columns are typically employed to perform this separation since, according to conventional wisdom, the two separations are best performed at different pressures.

The second column 14 recovers a high octane product and lower octane branched hydrocarbons which may be recycled to the isomerization zone. The highest octane hydrocarbons entering column 14 tend to be the most volatile and are removed as a net overhead stream of line 15. These hydrocarbons include isopentane and dimethylbutane. They are collectively referred to as the product isomerate of the overall isomerization-adsorption process. A sidecut stream is removed from the column through line 16 and comprises the bulk of the lower octane and higher boiling isoparaffins, such as methylpentanes. A much smaller stream of $C_6$ and $C_7$ naphthenes is removed from the process through line 17 for other processing or for other uses. The recovered high octane isomerate of line 15 is suitable for blending into a naphtha boiling range motor fuel.

FIG. 2 illustrates the subject fractionation method for separating the raffinate stream of line 10 which is produced in the adsorption zone. This method produces product and recycle streams equivalent to the arrangement of FIG. 1, but requires only a single column. The raffinate stream of line 10 enters the column 18 at an upper portion of a lower fractionation section of the column. The entering hydrocarbons are separated in the column with the higher boiling compounds migrating downward in the liquid phase to the bottom portion of the column and the more volatile hydrocarbons entering the rising vapor phase. The vapor phase passes upward through an intermediate section of the column having two parallel fractionation chambers, each containing fractionation trays 19. This intermediate section of the column is divided into the two chambers by the substantially imperforate wall 33 which forms a fluid tight divider between the hemispherical fractionation chambers located in the left and right hand sides of the column.

The less volatile hydrocarbons continue downward through the lower full diameter section of the column. A portion of this liquid is removed in the liquid-phase side-cut product stream of line 25. The rate of removal of the low octane number isoparaffins via line 25 is carefully controlled to allow sufficient liquid to remain in the column to overflow the chimney device 26 and pass downward into a lowermost trayed section of the column. In the lowermost portion of the column additional fractional distillation occurs producing a bottoms stream removed through line 21. The bottoms stream is divided into a small net product stream of line 25 comprising the $C_6$ naphthenes and some $C_7$ hydrocarbons. The remainder of the bottoms stream passes through line 22 into the reboiler 23 to generate the heated stream passed through line 24 into the bottom of the fractionation column. This effects reboiling and vaporization to generate vapors which travel upward through the column. This drives vapor upward through the left hand hemispherical chamber of the column formed by the wall 33. These vapors continue on upward and exit through a chimney 26 into the upper full diameter section of the column, which contains full size fractionation trays 19. Among the light components passing upward into the upper section of the column are the desorbent materials present in line 10, the highest octane highly branched isoparaffins which are collected as the isomerate and the low octane number isoparaffins which are recovered in line 16 of FIG. 1.

An overhead vapor stream is removed from column 18 in line 34 and passed through the overhead condenser 35 which results in at least partial condensation of the vapor. The overhead material then continues to flow through line 34 into the overhead receiver 36. The overhead liquid is removed through line 37 and divided into a net overhead product withdrawn through line 38 and a reflux stream returned to the column through line 39. The flow rate of each of these streams is regulated by valves and systems not shown which may be of totally conventional design. The liquid withdrawn in line 38 is rich in $C_4$ hydrocarbons which were employed as desorbent in the adsorptive separation zone and is therefore recycled to the adsorptive separation zone.

At the bottom of this upper section of the column a second trap out tray is used to remove a side draw stream through line 27. The stream of line 27 will contain the desired high octane number $C_5$–$C_6$ hydrocarbons which are to be recovered as the isomerate stream. A first portion of the stream of line 27 is returned to the column via line 28 at a rate controlled by valve 29 and refluxed to the left hand hemispherical chamber. The remaining portion of the liquid removed through line 27 is passed through line 30 and fed into the right hand hemispherical chamber of the column at a rate controlled by valve 31. The left and right hand chambers of the intermediate portion of the column both contain a plurality of evenly spaced fractional distillation trays 19 of conventional design. The tray spacing, layout and type of tray may vary between the two chambers. As in the other portions of the column the liquid fed to the top of the right hand chamber passes downward and is subjected to fractional distillation promoted by the generation of vapors in the bottom of the chamber by a reboiler means not shown. This reboiler may be a heat exchanger located within the column. Alternatively a portion of a side draw liquid removed through line 32 can be passed into a separate external heat exchanger located outside of the column 18, with the heated and possibly partially vaporized material then being returned to the column. In any event there is produced a side draw material removed through line 32 which is stripped of light materials, such as desorbent, and is a suitable high octane blending component for naphtha boiling range motor fuels.

The table below sets out the octane numbers, both research octane (RON-C) and motor octane (MON-C) of some representative components of a $C_5$–$C_6$ motor fuel isomerate. This information is presented to show the range between such low octane materials as n-pentane and n-hexane and high octane materials, such as the dimethyl butanes. The mono-branched materials have an intermediate octane. As used herein the term high octane is intended to indicate an octane number (R&M/2) by ASTM methods greater than 86. Low octane is similarly defined as less than 80.

Octane Numbers of Some Pure Components

|  | ASTM | |
|---|---|---|
|  | RON-C | MON-C |
| $C_5$: | | |
| i-Pentane | 92.3 | 90.3 |
| n-Pentane | 61.7 | 62.6 |

Octane Numbers of Some Pure Components -continued

|  | ASTM | |
|---|---|---|
|  | RON-C | MON-C |
| $C_6$: | | |
| 2,2-Dimethylbutane | 91.8 | 93.4 |
| 2,3-Dimethylbutane | 103.5 | 94.3 |
| 2-Methylpentane | 73.4 | 73.5 |
| 3-Methylpentane | 74.5 | 74.3 |
| n-Hexane | 24.8 | 26.0 |
| Methylcyclopentane | 91.3 | 80.0 |
| Cyclohexane | 83.0 | 77.2 |
| Benzene | 120.0 | 115.0 |

As an example of the use of the subject invention, based upon engineering calculations and past operational experience of prior art columns, a raffinate stream from a simulated continuous moving bed adsorptive separation zone would enter the column at tray number 40 of an 80 tray column. This tray would be immediately below the intermediate section of the column, which is divided into two parallel fractionation chambers by a vertical wall. The example is therefore similar to the depiction of FIG. 2. The left hand fractionation chamber is larger in cross-sectional area and contains 20 trays. The product producing right hand chamber also contains 20 trays. An additional 20 full diameter trays are employed in the upper section of the column. The lower section of the column is divided into two 20 tray sub-sections by the trap out tray used to collect a low octane sidecut product. The lowermost twenty trays receive a portion of the sidecut as reflux and produce a small net bottoms of $C_6$ naphthenes and $C_7$ hydrocarbons. The left hand, or non-product producing, chamber has a larger cross-sectional area to accommodate a higher vapor flow rate. The non-product chamber is expected to occupy between 50 to about 70 percent of the column's cross-sectional area, at this point in the column. The column's diameter could vary along its height, but this is not preferred.

The subject process may accordingly be characterized as a process for isomerization of a feed stream comprising normal paraffins having between 5 and 7 carbon atoms per molecule, which process comprises passing the feed stream and a hereinafter characterized recycle stream into a paraffinic hydrocarbon isomerization zone in which the feed stream is contacted with an isomerization catalyst at isomerization conditions to yield an isomerization zone effluent stream comprising normal, mono-branched and di-branched paraffins; passing the isomerization zone effluent stream into an adsorption zone in which the isomerization zone effluent stream contacts an adsorbent which is selective for normal paraffins to yield an adsorption zone raffinate stream which comprises mono-branched paraffins, di-branched paraffins and a desorbent hydrocarbon having less than six carbon atoms per molecule; passing the adsorption zone raffinate stream into a fractionation column maintained at fractionation conditions and comprising upper, lower and intermediate fractionation sections, with the intermediate fractionation section being divided into first and second vertical and parallel fractionation chambers by a vertical wall, the fractionation chambers having upper and lower ends, and with the second fractionation chamber being substantially sealed at its lower end and operated as a stripping zone; recovering an overhead stream comprising the desorbent hydrocarbon from the upper fractionation section, recycling at least a first portion of the overhead stream to the adsorption zone and refluxing a second portion of the overhead steam to the upper fractionation section of the column; passing liquid phase hydrocarbons downward from the upper fractionation section of the column into the first and second fractionation chambers; withdrawing a first process stream comprising di-branched paraffins from a lower portion of the second fractionation chamber; and, withdrawing a second process stream, which is rich in mono-branched paraffins, from a lower portion of the lower fractionation section of the column, and recycling at least a portion of the second process stream to the isomerization zone as the recycle stream.

What is claimed:

1. A process for recovering high octane, di-branched paraffins from the raffinate stream of an adsorptive separation process, which process comprises a.) passing a raffinate stream removed from an adsorptive separation zone, which stream comprises a desorbent hydrocarbon, mono-branched paraffins and di-branched paraffins, into a fractional distillation column maintained at fractionation conditions, with said column having an intermediate section divided into adjoining first and second vertical fractionation chambers by a substantially flow preventing vertical dividing wall, with the column also containing an upper first full diameter fractionation section located above the intermediate section and a lower second full diameter fractionation section located below the intermediate section;

b.) recovering a first product stream rich in mono-branched paraffins from the second full diameter fractionation section;

c.) allowing vapor to pass upward from the second full diameter fractionation section into the first vertical fractionation chamber, and allowing vapor to pass upward from the first vertical fractionation chamber into the first full diameter fractionation section;

d.) removing an overhead vapor stream comprising the desorbent hydrocarbon from the first full diameter fractionation section, and recovering a second product stream comprising the desorbent hydrocarbon;

e.) passing liquid comprising di-branched paraffins and the desorbent hydrocarbon downward from the first full diameter fractionation section into the second vertical fractionation chamber;

f.) recovering a second product stream comprising di-branched paraffins from a lower portion of the second vertical fractionation chamber.

2. The process of claim 1 further characterized in that the di-branched paraffins have 5 to 7 carbon atoms per molecule.

3. The process of claim 2 further characterized in that the desorbent hydrocarbon is butane.

4. The process of claim 1 further characterized in that the raffinate stream is removed from a simulated moving bed adsorptive separation zone.

5. The process of claim 1 further characterized in that at least a portion of the di-branched paraffins.are produced in an isomerization zone.

6. The process of claim 1 further characterized in that the first vertical fractionation chamber of the intermediate section of the column has a cross-sectional area equal to 50–70 percent of the cross-section of the column.

* * * * *

UNITED STATES PATENT AND TRADEMARK OFFICE
CERTIFICATE OF CORRECTION

PATENT NO. : 6,552,242 B1
DATED : April 22, 2003
INVENTOR(S) : Lynn H. Rice

It is certified that error appears in the above-identified patent and that said Letters Patent is hereby corrected as shown below:

Column 6,
Line 51, the number "25" should be replaced with the number -- 45 -- and also in
Line 60, the number "26" should be replaced with the number -- 46 --.

Column 9,
Line 16, the word "the" should be replaced with the word -- a -- and
Line 17, the word "which" should be replaced with the word -- said -- and the word "comprises" should be replaced with the word -- comprising --.
Line 18, the word "a" should be replaced with the word -- the --.

Column 10,
Line 14, the word -- and -- should be inserted after the semi-colon.
Line 15, the word "second" should be replaced with the word -- third --.

Signed and Sealed this

Nineteenth Day of August, 2003

JAMES E. ROGAN
*Director of the United States Patent and Trademark Office*